United States Patent
Fujiyama et al.

(10) Patent No.: US 10,639,268 B2
(45) Date of Patent: May 5, 2020

(54) OILY COSMETIC

(71) Applicant: SHISEIDO COMPANY, LTD., Tokyo (JP)

(72) Inventors: Nozomi Fujiyama, Yokohama (JP); Yukie Yoda, Yokohama (JP); Kazuyuki Miyazawa, Yokohama (JP); Nobuyuki Ide, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/329,081

(22) PCT Filed: Jul. 28, 2015

(86) PCT No.: PCT/JP2015/071348
§ 371 (c)(1),
(2) Date: Jan. 25, 2017

(87) PCT Pub. No.: WO2016/017624
PCT Pub. Date: Feb. 4, 2016

(65) Prior Publication Data
US 2017/0224608 A1 Aug. 10, 2017

(30) Foreign Application Priority Data

Jul. 28, 2014 (JP) ................... 2014-153240

(51) Int. Cl.
*A61K 8/90* (2006.01)
*A61Q 1/10* (2006.01)
*A61K 8/73* (2006.01)
*A61K 8/86* (2006.01)

(52) U.S. Cl.
CPC .............. *A61K 8/90* (2013.01); *A61K 8/73* (2013.01); *A61K 8/86* (2013.01); *A61Q 1/10* (2013.01); *A61K 2800/31* (2013.01)

(58) Field of Classification Search
None
See application file for complete search history.

(56) References Cited

U.S. PATENT DOCUMENTS

| 2003/0086887 A1* | 5/2003 | De La Poterie | A61K 8/37 424/70.11 |
| 2010/0048886 A1* | 2/2010 | Izume | A61K 8/73 536/123.1 |

FOREIGN PATENT DOCUMENTS

| JP | 5927328 | 4/1916 |
| JP | 2005 120057 | 5/2005 |
| JP | 2005120057 | 5/2005 |
| JP | 2005120057 A | * 5/2005 |
| JP | 2006-265216 | 10/2006 |
| JP | 2006 265216 | 10/2006 |
| JP | 2006265216 | 10/2006 |
| JP | 2006306849 | 11/2006 |
| JP | 5927328 | 4/2016 |
| WO | WO-2012133293 A1 | * 10/2012 ............... A61Q 1/10 |

OTHER PUBLICATIONS

English LanguageTranslation of JP 2005-120057 A (Year: 2005).*
English language translation of WO 2012/133293 A1. (Year: 2012).*
Japanese Appln. No. 2015-148462, Notice of Allowance dated Apr. 5, 2016, 3 pages—English (Certificate of Translation), 3 pages—Japanese.
Japanese Appln. No. 2015-148462, English translation of Japanese Patent claims as allowed, 1 page—English with Certificate of Translation.
Japanese Appln. No. 2015-148462, Notification of Reasons for Refusal, dated Oct. 20, 2015, 2 pages—English, 2 pages—Japanese.
PCT/JP2015/071348, International Search Report dated Oct. 27, 2015. 1 page—English, 2 pages—Japanese.
PCT/JP2015/071348, International Preliminary Report on Patentability dated Jan. 31, 2017, 1 page—English, 5 pages—Japanese.
PCT/JP2015/071348, Written Opinion dated Oct. 27, 2015, 5 pages—English, 4 pages—Japanese.
JP 2015-148462, Argument dated Dec. 21, 2015, 8 pages—English, 9 pages—Japanese.
PCT/JP2015/071348, International Search Report and Written Opinion, dated Oct. 27, 2015, 6 pages—Japanese; pages—English.
EP 15826324.4, Extended European Search Report dated Jan. 12, 2018, 6 pages English.

(Continued)

*Primary Examiner* — Dominic Lazaro
(74) *Attorney, Agent, or Firm* — Andrew F. Young, Esq.; Lackenbach Siegel, LLP

(57) ABSTRACT

The present invention provides an oil-based cosmetic that can easily be washed out with warm water and is excellent in water resistance. The oil-based cosmetic of the present invention is characterized by comprising (a) to (c):

(a) 1 to 25 mass % of a block-type alkylene oxide derivative represented by the below-described formula (I)

(b) 1 to 15 mass % of a siliconized pullulan and/or trimethylsiloxysilicic acid (c) 10 mass % or less of water $$R^1O-[(EO)_p(PO)_q(EO)_r]-R^2 \qquad (I)$$

(In the above formula, EO is an oxyethylene group and PO is an oxypropylene group. The symbols p, q, and r are the average addition mole numbers, and they are $p \geq 1$, $r \geq 1$, $10 \leq p+r \leq 70$, and $10 \leq q \leq 60$. $R^1$ and $R^2$ are either identical or different and they are either a hydrogen atom or a hydrocarbon group having 1 to 3 carbon atoms.)

8 Claims, No Drawings

(56) References Cited

OTHER PUBLICATIONS

Database GNPD (online) Mintel: Mar. 2008 (Mar. 2008), "lash enamel glamor neo (bk999)", XP002776915, Database accession No. 882480 * paragraph (ingredients)*.

Databse GNPD (online) Mintel: Feb. 2010 (Feb. 2010), "Mascara integral", XP002776916, Database accession No. 1265712 *paragraph (ingredients)*.

Database GNPD (online) Mintel; Jan. 2011 (Jan. 2011), "mascara integral", XP002776917, Database accession No. 1480597 *paragaraph (ingredients)*.

Database GNPD (online) Mintel; Apr. 2013 (Apr. 2013), "Mascara Iron Curl", XP002776918, Database accession No. 2039660 *paragraph (ingredients)*.

Database GNPD (online) Mintel; Feb. 2009 (Feb. 2009), "Liner Crème Regard Intense", XP002776919, Database accession No. 1051420 *paragarpah (ingredients)*.

* cited by examiner

OILY COSMETIC

RELATED APPLICATIONS

This application relates to and claims priority from Ser. No. PCT/JP2015/071348 filed Jul. 28, 2015, the entire contents of which are incorporated by reference, which in turn claims the priority of Japanese Patent Application No. 2014-153240 filed on Jul. 28, 2014, which is incorporated herein by reference.

FIELD OF THE INVENTION

The present invention relates to an oil-based cosmetic, and in particular, relates to an oil-based cosmetic that is excellent in water resistance despite easily removable with warm water.

BACKGROUND OF THE INVENTION

Eyelash cosmetics represented by e.g., mascara etc. can provide the eyelashes with effects on looking thick and long therefor and voluminousness, and it is further desirable if the effects on additional functional aspects including such as curling (effect to curl up eyelashes), retaining curl (effect to maintain curls over time), and long-lasting looking (effect on water resistance and sebum resistance) could be provided. However, the stronger water resistance and or sebum resistance is, the more difficult the product is to be washed out, because of the increased resistance effect against water, even if applied cleansing cosmetics or facial cleanser, and as result, an eye makeup remover is necessary as for some products.

In recent years, eyelash cosmetics such as mascara that can be washed out with warm water is getting available without the use of such a strong remover, which is called a mascara capable of being removed effectively with warm water. For example, an oil-in-water type eyelash cosmetic, which can be easily removed with warm water or even water, is disclosed in Patent literature 1. According to Patent literature 1, the easy removal of the cosmetics with water or warm water was feasible by blending a liquid crystal, which is formed of a polyhydric alcohol and an amphiphilic material, into the oil phase. However, a curling effect of such oil-in-water eyelash cosmetic, which can be washed out with water or warm water, is inferior to the oil-based eyelash cosmetics. In addition, such oil-in-water cosmetics are not water resistance, so that the cosmetics can be ineffective due to falling off even with rain drops.

On the other hand, the oil-based mascara is excellent in curling, but it is difficult to wash out with water or even warm water.

In addition, a mascara composition containing a specific alkylene oxide derivative and a film-forming agent is disclosed (Patent literature 2). Such mascara composition is not deemed as an oil-based eyelash cosmetic, so that such cosmetics can be further improved as for curling effect.

Oil-based cosmetics other than oil-based eyelash cosmetics are generally excellent in water resistance, but a drawback of such cosmetics makes the makeup left difficult to be washed out unless a makeup remover is used. Accordingly, it is desired to be developed that an oil-based cosmetic capable of being removed with warm water despite having an excellent water resistance becomes available.

Patent literature 1: Japanese unexamined patent publication No. 2006-306849

Patent literature 2: Japanese unexamined patent publication No. 2005-120057

DISCLOSURE OF THE INVENTION

Problem to be Solved by the Invention

The present invention was made in view of the above-described conventional art. An object of the invention is to provide an oil-based cosmetic that can be washed out exceptionally with warm water despite excellent water resistance.

Means to Solve the Problem

The present inventors have diligently studied to solve the above-described problem. As a result, the present inventors have found that an oil-based cosmetic is obtained by blending specific amount of (a) specific block-type alkylene oxide derivative and (b) siliconized pullulan and/or trimethylsiloxysilicic acid, which can be effectively washed out with warm water while keeping excellent water resistance, and excellent curling effect, and, thus leading to the completion of the present invention.

That is, the oil-based cosmetic of the present invention comprises:
(a) 1 to 25 mass % of a block-type alkylene oxide derivative represented by the following chemical formula (I)
(b) 1 to 15 mass % of a siliconized pullulan and/or trimethylsiloxysilicic acid
(c) 10 mass % or less of water

[Chemical Formula I]

$$R^1O-[(EO)_p(PO)_q(EO)_r]-R^2 \quad (I)$$

(In the above Chemical formula, EO is an oxyethylene group and PO is an oxypropylene group. The symbols p, q, and r are the average addition mole numbers, and $p \geq 1$, $r \geq 1$, $10 \leq p+r \leq 70$, and $10 \leq q \leq 60$ exist. $R^1$ and $R^2$ are either identical or different and they are either a hydrogen atom or a hydrocarbon group having 1 to 3 carbon atoms.)

In the above oil-based cosmetic, it is preferred that $R^1$ and $R^2$ of the block-type alkylene oxide derivative represented by Chemical formula (I) are hydrocarbon groups having 1 to 3 carbon atoms.

In the above oil-based cosmetic, it is preferred that a volatile oil is contained.

The oil-based eyelash cosmetic of the present invention comprises the above oil-based cosmetic.

The makeup method of the present invention comprises steps of applying the above cosmetic on the skin and washing out the cosmetic by rinsing with warm water at 35 to 45° C.

Effect of the Invention

The present invention can provide an oil-based cosmetic that can be effectively washer out with while having excellent water resistance.

In addition, when the oil-based cosmetic of the present invention is applied to an oil-based eyelash cosmetic, such oil-based eyelash cosmetic provides the eyelash with an excellent curling effect.

BEST MODE FOR CARRYING OUT THE INVENTION

The oil-based cosmetic of the present invention is an oil-based cosmetic, wherein specific amounts of (a) a block-type alkylene oxide derivative represented by formula (I) and (b) a siliconized pullulan and/or trimethylsiloxysilicic acid are blended, and such oil-based cosmetic is effectively washed out with warm water, while providing curling effect and water resistance. In the present invention, warm water means the water that has water temperature about 35 to 45° C., at which when touched water, water is felt as slightly warm.

In the following, each component is described in detail.

((a) Block-Type Alkylene Oxide Derivative)

The block-type alkylene oxide derivative is a compound represented by the Chemical formula (I).

[Chemical Formula I]

$$R^1O-[(EO)_p(PO)_q(EO)_r]-R^2 \qquad (I)$$

In the above formula (I), EO is an oxyethylene group and PO is an oxypropylene group. The symbols p, q, and r are the average addition mole numbers, and they are $p \geq 1$, $r \geq 1$, $10 \leq p+r \leq 70$, and $10 \leq q \leq 60$. If the content of oxyethylene groups or oxypropylene groups is too little, the effectiveness of washing out with warm water is poor; but if too much, the feeling-in-use thereof is poor.

Specific examples of alkylene oxide derivatives of the present invention include POE(35)POP(40)dimethyl ether, POE(50)POP(40)dimethyl ether, POE(22)POP(40)dimethyl ether, POE(55)POP(30)dimethyl ether, POE(30)POP(34)dimethyl ether, POE(25)POP(30)dimethyl ether, POE(36)POP(41)dimethyl ether, POE(52)POP(32)dimethyl ether, and POE(35)POP(32)dimethyl ether.

The above-described POE and POP are the abbreviations of polyoxyethylene and polyoxypropylene, respectively. Hereinafter, they may be abbreviated as such.

Component (a) forms micelles in the oil-based cosmetic of the present invention. When hot water is put on the skin where the oil-based cosmetic of the present invention is applied, the micelles break down with hot water and the cosmetic can be easily removed.

The blending quantity of (a) block-type alkylene oxide derivative is 1 to 25 mass % and preferably 3 to 20 mass %. If the blending quantity is less than 1 mass %, the hot-water removal effect is poor because of low micelle formation. If the blending quantity exceeds 25 mass %, stickiness is generated.

((b) Siliconized Pullulan and/or Trimethylsiloxysilicic Acid)

The siliconized pullulan is a compound represented by the below-described Chemical formula (II).

[Chemical Formula II]

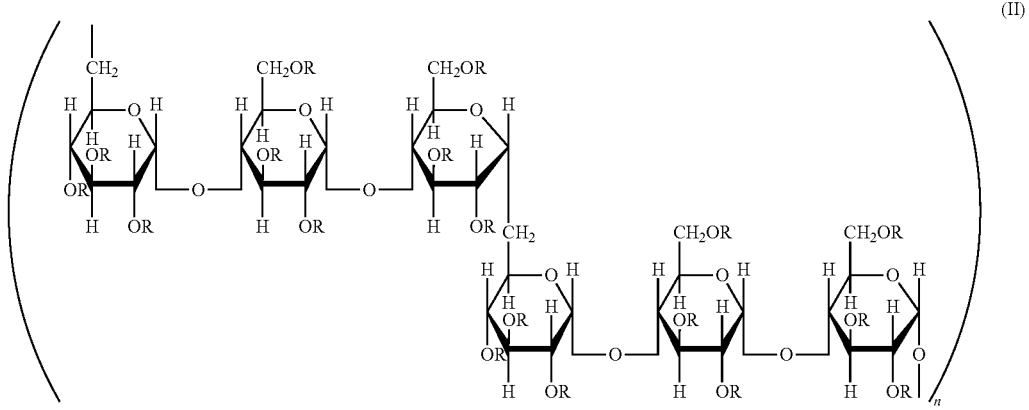

$R^1$ and $R^2$ are a hydrogen atom or a hydrocarbon group having 1 to 3 carbon atoms. Examples of hydrocarbon groups include methyl group, ethyl group, n-propyl group, and isopropyl group.

$R^1$ and $R^2$ are preferably a hydrocarbon group having 1 to 3 carbon atoms and more preferably methyl group. In the case of a hydrocarbon group having 4 or more carbon atoms, hydrophilicity is lowered and the hot-water removal effect tends to be poor.

For the respective $R^1$ and $R^2$, the same kinds may be used or different kinds may be mixed.

Block-type alkylene oxide derivative of the present invention can be produced by a publicly known method. For example, they can be obtained by the addition polymerization of an ethylene oxide and a propylene oxide to a compound having hydroxyl group and by performing an ether reaction with an alkyl halide in the presence of an alkaline catalyst.

In the above formula (II), R means a hydrogen atom or $[(CH_3)_3SiO]_3Si(CH_2)_3NHCO$.

In the siliconized pullulan, the bonding rate of silicone compounds to the reactive functional groups of pullulan varies depending upon the kinds thereof; normally, the average number of bonded silicone compounds per constituent sugar unit of the polysaccharide compound (degree of substitution) is preferably 0.5 to 3.0. In the present invention, the degree of substitution was calculated from the Si content (mass %) in the compound.

When the siliconized pullulan is blended, the ease of blending and the feeling in use can be improved if dissolved in a low-molecular-weight silicone oil or a light isoparaffin.

The preferable siliconized pullulan used in the present invention is tri(trimethylsiloxy)silylpropylcarbamic acid-pullulan represented by the following Chemical formula (III).

[Chemical Formula III]

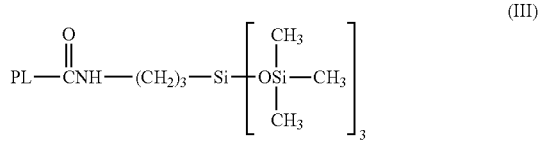

In the above formula (III), PL represents the glucose residues of pullulan.

Siliconized pullulan produced by a publicly known preparation method can be used (for example. Japanese unexamined patent publication No. H10-29910).

Examples of commercial products include TSPL-30-ID (tri(trimethylsiloxy)silylpropylcarbamic acid-pullulan, produced by Shin-Etsu Chemical Co., Ltd., 30% isododecane solution) and TSPL-30-D5 (tri(trimethylsiloxy)silylpropylcarbamic acid-pullulan, produced by Shin-Etsu Chemical Co., Ltd., 30% decamethylcyclopentasiloxane solution).

Trimethylsiloxysilicic acid produced by a publicly known preparation method can be used.

Examples of commercial products include SSD-R2 (produced by Shin-Etsu Chemical Co., Ltd., 30% decamethylcyclopentasiloxane solution), MQ-1600 Solid Resin (produced by Dow Corning Toray Co., Ltd., purity: 100%), and Wacker-Belsil TMS803 (produced by Wacker Asahikasci Silicone Co., Ltd., purity: 100%).

The blending quantity of (b) a siliconized pullulan and/or trimethylsiloxysilicic acid is 1 to 15 mass %, as the net amount, and preferably 2 to 8 mass %. If the blending quantity of the film-forming agent is less than 1 mass %, effective washing out with warm water, durability of makeup, and curling effect are poor. If the blending quantity exceeds 15 mass %, curling effect is poor.

((c) Water)

In the present invention, water may or may not be blended; when blended, water is stably present in the micelle that is formed by component (a).

In the present invention, it is necessary that the blending quantity of water is 10 mass % or less with respect to the total cosmetic. The blending quantity is preferably 5 mass % or less and more preferably 3 mass % or less with respect to the total cosmetic.

If the blending quantity of water is too much, it becomes difficult to take into the micelle that is formed by component (a); and thus it is not desirable. Furthermore, the application becomes difficult when it is formulated into an oil-based eyelash cosmetic.

By blending the above components (a) to (c), an oil-based cosmetic that can be effectively washed out while having water resistance and the curling effect can be obtained.

Examples of other blending components include oil such as volatile oil, wax, dextrin fatty acid ester, organic-modified clay mineral, coloring material, etc.

Examples of volatile oils include hydrocarbon oils such as light liquid paraffin and isododecane, chain polysiloxane oils such as low molecular weight volatile dimethylpolysiloxane, and cyclic silicone oils such as octamethylcyclotetrasiloxane, decamethylcyclopentasiloxane, and dodecamethylcyclohexasiloxane.

The blending quantity of volatile oil is preferably 10 to 80 mass % and more preferably 30 to 60 mass %. If the blending quantity of the volatile oil is less than 10 mass %, the application may become difficult. If the blending quantity exceeds 80 mass %, viscosity may not be maintained.

Examples of oils include hydrocarbon oils such as heavy isoparaffin, squalane, and liquid paraffin; esters such as cetyl-2-ethylhexanoate, 2-ethylhexyl palmitate, 2-octyldodecyl myristate, neopentylglycol-2-ethylhexanoate, and isopropyl myristate; fats such as olive oil, avocado oil, jojoba oil, sunflower oil, safflower oil, camellia oil, macadamia nut oil, mink oil, liquid lanorin, lanorin acetate, castor oil; silicone oils such as dimethylpolysiloxane, methylphenyl polysiloxane, high polymerization degree gumlike dimethylpolysiloxane, polyether-modified silicone, and amino-modified silicone; fluorinated oils such as fluorine-modified dimethylpolysiloxane, fluorine-modified methylphenyl polysiloxane, perfluoropolyether, and perfluorocarbon.

Examples of waxes include beeswax, candelilla wax, cotton wax, carnauba wax, bayberry wax, insect wax, whale wax, montan wax, bran wax, lanolin, kapok wax, lanolin acetate, liquid lanolin, sugar cone wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, POE hydrogenated lanolin alcohol ether, ceresin, polyethylene wax, microcrystalline wax, sugar wax, and paraffin wax.

The blending quantity of wax is preferably 1 to 20 mass % and more preferably 3 to 15 mass %. If the blending quantity of the wax is less than 1 mass %, the curling effect may be poor. If the blending quantity exceeds 20 mass %, lumps are formed and adherence may become poor.

As the dextrin fatty acid ester, ester compounds of a fatty acid of 8 to 24 carbon atoms and a dextrin with the average degree of polymerization of 10 to 50 are preferable. Examples include dextrin palmitate, dextrin stearate, dextrin palmitate stearate, dextrin isostearate, and dextrin (palmitate/2-ethylhexanoate).

The blending quantity of the dextrin fatty acid ester is preferably 1 to 15 mass % and more preferably 3 to 10 mass %. If the blending quantity of dextrin fatty acid ester is less than 1 mass %, stability may be poor. If the blending quantity exceeds 15 mass %, uniform application may not be possible.

Organic-modified clay minerals can be obtained by treating clay minerals such as natural or synthetic montmorillonites, for example, montmorillonite, saponite, and hectorite (commercial products are Veegum, Kunipia, Laponite, etc.) or synthetic micas known as sodium silicic mica and sodium or lithium taeniolite, with a quaternary ammonium salt-type cationic surfactant. Examples include disteardimonium hectorite, dimethylalkylammonium hectorite, distearyldimethylammonium chloride-treated magnesium aluminum silicate, etc.

The blending quantity of the organic-modified clay mineral is preferably 1 to 10 mass % and more preferably 2 to 8 mass %. If the blending quantity of clay mineral is less than 1 mass %, thixotropy may not be obtained. If the blending quantity exceeds 10 mass %, uniform application may not be possible.

The coloring material is not limited in particular so far as it is generally used in makeup cosmetics; however, a hydrophobic material is preferably used. Examples of coloring materials include red zinc oxide, yellow zinc oxide, black zinc oxide, inorganic white family pigment (for example, zinc oxide); inorganic red family pigment (for example, iron titanate); inorganic purple family pigment (for example, mango violet, cobalt violet); inorganic green family Pigment (for example, chrome oxide, chrome hydroxide, cobalt titanate); inorganic blue family pigment (for example, ultramarine, iron blue); pearl pigment (for example, titanium oxide coated mica, titanium oxide coated bismuth oxychloride, titanium oxide coated talc, colored titanium oxide coated mica, bismuth oxychloride, argentine); metal powder pigment (for example, aluminum powder, and copper powder); organic pigment such as zirconium, barium, or aluminum lake (for example, organic pigment such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, or Red No. 3, Red No. 104, Red No. 106, Red No. 227, Red No. 230, Red No. 401, Red No. 505, Orange No. 205, Yellow No. 4, Yellow No. 5, Yellow No. 202. Yellow No. 203, Green No. 3, and Blue No. 1); natural pigment (for example, chlorophyll, and □-carotene).

The blending quantity of the coloring material is preferably 1 to 30 mass % and more preferably 2 to 20 mass %.

Moreover, in the oil-based cosmetic of the present invention, a film-forming agent other than component (b), a fiber, a moisturizer, a drug, a preservative agent, a thickening agent, a perfume, an antioxidizing agent, an UV absorber, and the like can be blended within the range that the effect of the present invention is not impaired.

Even when a film-forming agent other than component (b) is blended, the effect of the present invention cannot be obtained. However, a film-forming agent other than component (b) can be blended within the range that the effect of the present invention is not impaired.

Examples of film-forming agents other than component (b) include dimethylamino methacylate quaternized salt, vinyl pyrrolidone/methacrylate-N,N-dimethyl-ethyl antinioethyl salt copolymer, silicone/polyether-type polyurethane resin, (methacryloyloxy ethyl carboxybetaine/methacryl alkyl) copolymer, dextrin, (vinyl pyrrolidone/VA) copolymer, alkyl acrylate copolymer ammonium, polyvinyl alcohol, ethyl acrylate, (alkyl acrylate/octyl acrylamide) copolymer, (acrylate/propyltrimethicone methacrylate) copolymer, vinyl polyacetate, (alkyl acrylate/dimethicone) copolymer, polyether graft acryl silicone, trimethylsiloxysilicic acid, and fluoro-modified silicone resin.

The oil-based cosmetic of the present invention can be widely applied. For example, it can be applied to eyelash cosmetic such as mascara and mascara base, makeup cosmetic such as lip gross, eye shadow, blusher, foundation, and eye liner, skincare cosmetic such as beauty essense, milky lotion, cream, and pack, nail enamel, hair wax, spray, and mousse.

Among them, the oil-based cosmetic of the present invention is preferably an oil-based eyelash cosmetic because it is also excellent in the curling effect.

The oil-based cosmetic of the present invention does not fall off or deteriorates, so far as pressing is light, even when it gets wet with sweat or water at a temperature lower than the warm water temperature.

On the other hand, when warm water is used, the oil-based cosmetic can be washed out from the skin by simply rubbing with a finger or palm; therefore, the removal of makeup can be accomplished only by washing with warm water but no cleansing cosmetics such as makeup remover or cleansers like facial cleanser is needed. When the oil-based cosmetic is being washed out, cloth, gauze, cotton, etc. soaked with warm water can be workable also.

In the present invention, warm water is water having temperature about 35 to 45° C.; however, from the standpoint of burden to the skin and thermal irritation, warm water is preferably about 40° C.

EXAMPLES

The present invention will be further described in the following examples. However, the invention is not limited by these examples. Unless otherwise specified, the blending quantity of each component will be expressed in mass %.

Prior to illustrating the examples, the methods for the evaluation tests used in the present invention will be explained.

In the evaluation methods below, a "plate" means the one obtained by the following method.

(Preparation Method of a Plate)

By machining a copper plate (steel material), groove-like concave sections with a width of 300 µm, a depth of 80 µm, and V-shaped cross section were formed, 1 piece/2 mm in the longitudinal direction, 1 piece/1 mm in the lateral direction, and 2 pieces/3 mm in the 45° diagonal direction; thus a 50-mm-square primary master was prepared. The primary mold was prepared by electroforming the primary master with nickel. With the use of the primary mold, PMMA, namely Acrypet VH000 (manufactured by Mitsubishi Rayon Co., Ltd.) was injection molded. The secondary master was prepared, via sand blasting process, by blasting white fused alumina abrasive, Fuji Rundum WA, particle size #80 (manufactured by Fuji Manufacturing Co., Ltd.), with a sand blaster PNEUMA BLASTER (manufactured by Fuji Manufacturing Co., Ltd.), on the surface of the obtained molded article on the side where groove-like concave sections were formed. With the use of the secondary master, metal resin was molded; thus the secondary mold, wherein the convex sections are chamfered and chamfered roughness is provided on the planar section, was prepared. With the use of the secondary mold, Acrypet VH000 (manufactured by Mitsubishi Rayon Co., Ltd.) was injection molded; thus a plate (skin substitute membrane) was prepared.

Evaluation (1): Hot-Water Removal Effect

A sample (0.04 g) was applied on a plate (5 cm×5 cm), dried at room temperature for 5 hours, and rubbed by hand with warm water at 40° C.; washed-out sample from the plate was observed and evaluated by the following criteria.

S: Washed out completely by slightly rubbing
A: Washed out by rubbing
B: Washed out by firmly rubbing but not by lightly rubbing
C: Not washed out at all even by firmly rubbing Evaluation (2): Water Resistance A sample (0.04 g) was applied on a plate (5 cm×5 cm) and dried at room temperature for 5 hours. The immersion of the obtained film, together with the plate, into water at 25° C. and the immediate lifting were repeated 10 times, and the removal or deterioration of the film was observed by the naked eye (immediately after immersion). In addition, after allowing to stand at room temperature (25° C.) for 1 minute, removability or damage of the film by light finger rubbing was observed by the naked eye (when rubbed).

S: Nothing is removed from the plate or no damage is observed, at all.
A: The film is hardly removed and somewhat damage is observed.
B: The film is removed or damaged by rubbing.
C: Immediately after the film is immersed in water, the film is removed or damaged.

Evaluation (3): Curling Effect

Five expert panelists applied a sample on the eyelashes 30 times, and the curling effect immediately after application was compared with the curling effect when the formulation X (oil-in-water mascara cosmetic) was similarly applied; thus evaluation was carried out.

A: Four panelists or more evaluated that the curling effect of the sample was higher.
B: Three panelists or less evaluated that the curling effect of the sample was lower.

Formulation X

| POE(36)POP(41) dimethylether (block-type) | 5% by mass |
|---|---|
| Vinyl acetate emulsion | 20 |
| Carnauba wax | 5 |
| Beeswax | 8 |
| Stearic acid | 2 |
| Bentonite | 2 |
| Liquid paraffin | 3 |
| Sodium carboxymethyl cellulose (low viscosity) | 0.2 |
| Sodium lauryl sulfate | 0.1 |
| Carbon Black | 1.5 |
| Phenoxy ethanol | 5 |
| Purified water | balance |

In the oil-based eyelash cosmetic having a high curling effect, additive components that allow easy removal with warm water were investigated.

The present inventors prepared the samples (oil-based mascara) shown in Table 1 below by the ordinary method based on the hypothesis that the break-down of an oil-based film with hot water becomes possible if micelles are formed in the oil-based film. The respective samples were evaluated by the above-described evaluation methods (1) to (3).

In the following examples, unless otherwise described, a block polymer was used as the POE/POP dimethyl ether. The results are shown in Table 1.

TABLE 1

| | Test Example | | | |
|---|---|---|---|---|
| | 1-1 | 1-2 | 1-3 | 1-4 |
| POE(35)POP(40) dimethylether | — | 10.0 | — | — |
| POE(50)POP(40) dimethylether | — | — | 10.0 | — |
| Carboxyvinylpolymer | — | — | — | 1.0 |
| Tri(trimethylsiloxy)silylpropylcarbamic acid-pullulan | 3.5 | 3.5 | 3.5 | 3.5 |
| Isododecane | 8.5 | 8.5 | 8.5 | 9.0 |

TABLE 1-continued

| | Test Example | | | |
|---|---|---|---|---|
| | 1-1 | 1-2 | 1-3 | 1-4 |
| Hydrogenated polyisobutene | 49.0 | 39.0 | 39.0 | 40.0 |
| Wax | 8.0 | 8.0 | 8.0 | 8.0 |
| Dextrin palmitate | 8.0 | 8.0 | 8.0 | 8.0 |
| Dextrin (palmitate/2-ethylhexanoate) | 1.5 | 1.5 | 1.5 | 1.5 |
| Organic-modified bentonite | 4.0 | 4.0 | 4.0 | 4.0 |
| PEG-10 dimethicone | 4.0 | 4.0 | 4.0 | 4.0 |
| Hydrophobized iron oxide | 5.0 | 5.0 | 5.0 | 5.0 |
| Water | 3.0 | 3.0 | 3.0 | 10.5 |
| Butylene glycol | 2.0 | 2.0 | 2.0 | 2.0 |
| Niron fiber | 2.5 | 2.5 | 2.5 | 2.5 |
| Mica | 0.5 | 0.5 | 0.5 | 0.5 |
| Hydrophobized pearl agent | 0.5 | 0.5 | 0.5 | 0.5 |
| Evaluation (1): Effective washing out with warm water | C | S | S | C |
| Evaluation (2): Water resistance | A | A | A | C |
| Evaluation (3): Curling effect | A | A | A | A |

As shown in Table 1, the warm water removal effect was excellent in Test Example 1-2, wherein the amphiphilic polymer POE(35)POP(40) dimethyl ether was blended into the oil-based mascara of Test Example 1-1 in which the high curling effect was Present.

In addition, the effective washing out with warm water was excellent in Test Example 1-3, wherein the amphiphilic polymer POE(50)POP(40) dimethyl ether was blended into the oil-based mascara of Test Example 1-1.

On the other hand, when a carboxyvinyl polymer was blended into the oil-based mascara of Test Example 1-1, the effective washing out with warm water was not present.

Subsequently, the kinds of amphiphilic polymers were investigated.

The present inventors prepared the samples (oil-based mascara) shown in Table 2 below by the ordinary method. The respective samples were evaluated by the above-described evaluation methods (1) to (3). The results are shown in Table 2.

TABLE 2

| Test Example | 1-2 | 1-3 | 2-1 | 2-2 | 2-3 | 2-4 | 2-5 | 2-6 | 2-7 | 2-8 | 2-9 |
|---|---|---|---|---|---|---|---|---|---|---|---|
| POE(35)POP(40) dimethylether | 10 | — | — | — | — | — | — | — | — | — | — |
| POE(50)POP(40) dimethylether | — | 10 | — | — | — | — | — | — | — | — | — |
| POE(10)POP(40) dimethylether | — | — | 10 | — | — | — | — | — | — | — | — |
| POE(70)POP(40) dimethylether | — | — | — | 10 | — | — | — | — | — | — | — |
| POE(27)POP(14) dimethylether | — | — | — | — | 10 | — | — | — | — | — | — |
| POE(35)POP(60) dimethylether | — | — | — | — | — | 10 | — | — | — | — | — |
| POE(36)POP(41) dimethylether (random polymer) | — | — | — | — | — | — | 10 | — | — | — | — |
| POE(3)POP(6) dimethylether | — | — | — | — | — | — | — | 10 | — | — | — |
| POE(17)POP(4) dimethylether | — | — | — | — | — | — | — | — | 10 | — | — |
| POE(14)POP(7) dimethylether | — | — | — | — | — | — | — | — | — | 10 | — |
| POE(100)POP(56) glycol (Pluronic) | — | — | — | — | — | — | — | — | — | — | 10 |
| Tri(trimethylsiloxy)silylpropylcarbamic acid-pullulan | 3.5 | 3.5 | 3.5 | 3.5 | 3.5 | 3.5 | 3.5 | 3.5 | 3.5 | 3.5 | 3.5 |
| Isododecane | 8.5 | 8.5 | 8.5 | 8.5 | 8.5 | 8.5 | 8.5 | 8.5 | 8.5 | 8.5 | 8.5 |
| Hydrogenated polyisobutene | 40 | 40 | 40 | 40 | 40 | 40 | 40 | 40 | 40 | 40 | 40 |
| Wax | 8 | 8 | 8 | 8 | 8 | 8 | 8 | 8 | 8 | 8 | 8 |
| Dextrin palmitate | 7 | 7 | 7 | 7 | 7 | 7 | 7 | 7 | 7 | 7 | 7 |
| Dextrin (palmitate/2-ethylhexanoate) | 1.5 | 1.5 | 1.5 | 1.5 | 1.5 | 1.5 | 1.5 | 1.5 | 1.5 | 1.5 | 1.5 |
| Organic-modified bentonite | 4 | 4 | 4 | 4 | 4 | 4 | 4 | 4 | 4 | 4 | 4 |
| PEG-10 dimethicone | 4 | 4 | 4 | 4 | 4 | 4 | 4 | 4 | 4 | 4 | 4 |
| Hydrophobized iron oxide | 5 | 5 | 5 | 5 | 5 | 5 | 5 | 5 | 5 | 5 | 5 |
| Water | 3 | 3 | 3 | 3 | 3 | 3 | 3 | 3 | 3 | 3 | 3 |

TABLE 2-continued

| Test Example | 1-2 | 1-3 | 2-1 | 2-2 | 2-3 | 2-4 | 2-5 | 2-6 | 2-7 | 2-8 | 2-9 |
|---|---|---|---|---|---|---|---|---|---|---|---|
| Butylene glycol | 2 | 2 | 2 | 2 | 2 | 2 | 2 | 2 | 2 | 2 | 2 |
| Niron fiber | 2.5 | 2.5 | 2.5 | 2.5 | 2.5 | 2.5 | 2.5 | 2.5 | 2.5 | 2.5 | 2.5 |
| Extender pigment | 0.5 | 0.5 | 0.5 | 0.5 | 0.5 | 0.5 | 0.5 | 0.5 | 0.5 | 0.5 | 0.5 |
| Hydrophobized pearl agent | 0.5 | 0.5 | 0.5 | 0.5 | 0.5 | 0.5 | 0.5 | 0.5 | 0.5 | 0.5 | 0.5 |
| Evaluation (1): Effective washing out with warm water | S | S | S | S | S | S | B | C | C | C | A |
| Evaluation (2): Water resistance | A | A | A | A | A | A | B | B | B | B | C |
| Evaluation (3): Curling effect | A | A | A | A | A | A | A | A | A | A | C |

As shown in Table 2, the effective washing out with warm water was found to be affected by the numbers of EO and PO in the block-type alkylene oxide derivative.

Furthermore, when a random-type alkylene oxide derivative or other amphiphilic polymers were blended, an oil-based mascara excellent in the effective washing out with warm water could not be obtained.

As a result of these investigation, it was clarified that a (a) block-type alkylene oxide derivative represented by $R^1O—[(EO)_p(PO)_q(EO)_r]—R^2$ needs to be contained in the oil-based cosmetic of the present invention (however, in the formula, EO is an oxyethylene group and PO is an oxypropylene group. The symbols p, q, and r are the average addition mole numbers, and they are $p \geq 1$, $r \geq 1$, $10 \leq p+r \leq 70$, and $10 \leq q \leq 60$. $R^1$ and $R^2$ are either identical or different and they are either a hydrogen atom or a hydrocarbon group having 1 to 3 carbon atoms.).

Subsequently, the blending quantity of (a) block-type alkylene oxide derivative was investigated.

The present inventors prepared the samples (oil-based mascara) shown in Table 3 below by the ordinary method. The respective samples were evaluated by the above-described evaluation methods (1) to (3). The results are shown in Table 3.

TABLE 3

| Test Example | 3-1 | 3-2 | 3-3 | 1-2 | 3-4 | 3-5 | 3-6 | 1-3 |
|---|---|---|---|---|---|---|---|---|
| POE(35)POP(40) dimethylether | 1 | 3 | 5 | 10 | — | — | — | — |
| POE(50)POP(40) dimethylether | — | — | — | — | 1 | 3 | 5 | 10 |
| Tri(trimethylsiloxy)silylpropylcarbamic acid-pullulan | 3.5 | 3.5 | 3.5 | 3.5 | 3.5 | 3.5 | 3.5 | 3.5 |
| Isododecane | 8.5 | 8.5 | 8.5 | 8.5 | 8.5 | 8.5 | 8.5 | 8.5 |
| Hydrogenated polyisobutene | 48 | 46 | 44 | 39 | 48 | 46 | 44 | 39 |
| Wax | 9 | 9 | 9 | 9 | 9 | 9 | 9 | 9 |
| Dextrin palmitate | 7 | 7 | 7 | 7 | 7 | 7 | 7 | 7 |
| Dextrin (palmitate/2-ethylhexanoate) | 1.5 | 1.5 | 1.5 | 1.5 | 1.5 | 1.5 | 1.5 | 1.5 |
| Organic-modified bentonite | 4 | 4 | 4 | 4 | 4 | 4 | 4 | 4 |
| PEG-10 dimethicone | 4 | 4 | 4 | 4 | 4 | 4 | 4 | 4 |
| Hydrophobized iron oxide | 5 | 5 | 5 | 5 | 5 | 5 | 5 | 5 |
| Water | 3 | 3 | 3 | 3 | 3 | 3 | 3 | 3 |
| Butylene glycol | 2 | 2 | 2 | 2 | 2 | 2 | 2 | 2 |
| Niron fiber | 2.5 | 2.5 | 2.5 | 2.5 | 2.5 | 2.5 | 2.5 | 2.5 |
| Extender pigment | 0.5 | 0.5 | 0.5 | 0.5 | 0.5 | 0.5 | 0.5 | 0.5 |
| Hydrophobized pearl agent | 0.5 | 0.5 | 0.5 | 0.5 | 0.5 | 0.5 | 0.5 | 0.5 |
| Evaluation (1): Effective washing out with warm water | B | A | S | S | B | A | A | S |
| Evaluation (2): Water resistance | A | A | A | A | A | A | A | A |
| Evaluation (3): Curling effect | A | A | A | A | A | A | A | A |

As shown in Table 3, the effect of addition was observed even with 1 mass % of a block-type alkylene oxide derivative. However, an oil-based mascara with a better effective washing out with warm water was found to be obtained by blending 3 mass % or higher thereof.

By allowing the blending quantity of (a) a block-type alkylene oxide derivative to be 1 to 25 mass %, the effective washing out with warm water can be obtained. In order to achieve a better effective washing out with warm water, the blending quantity of component (a) is preferably 3 mass % or higher, and more preferably 5 mass % or higher.

Subsequently, the kinds of film-forming agents were investigated.

The present inventors prepared the samples (oil-based mascara) shown in Table 4 below by the ordinary method. The respective samples were evaluated by the above-described evaluation methods (1) to (3). The results are shown in Table 4.

TABLE 4

|  | Test Example | | |
|---|---|---|---|
|  | 1-2 | 4-1 | 4-2 |
| POE(35)POP(40) dimethylether | 10 | 10 | 10 |
| Tri(trimethylsiloxy)silylpropylcarbamic acid-pullulan | 3.5 | — | — |
| Trimethylsiloxysilicate | — | 3.5 | 3.5 |
| Isododecane | 8.5 | 8.5 | — |
| Decamethylcyclopentasiloxane | — | — | 8.5 |
| Hydrogenated polyisobutene | 39 | 39 | 39 |
| Wax | 8 | 8 | 8 |
| Dextrin palmitate | 8 | 8 | 8 |
| Dextrin (palmitate/2-ethylhexanoate) | 1.5 | 1.5 | 1.5 |
| Organic-modified bentonite | 4 | 4 | 4 |
| PEG-10 dimethicone | 4 | 4 | 4 |
| Hydrophobized iron oxide | 5 | 5 | 5 |
| Water | 3 | 3 | 3 |
| Butylene glycol | 2 | 2 | 2 |
| Niron fiber | 2.5 | 2.5 | 2.5 |
| Extender pigment | 0.5 | 0.5 | 0.5 |
| Hydrophobized pearl agent | 0.5 | 0.5 | 0.5 |
| Evaluation (1): Effective washing out with warm water | S | S | S |
| Evaluation (2): Water resistance | A | A | A |
| Evaluation (3): Curling effect | A | B | B |

As shown in Table 4, even when the siliconized pullulan, which is a film-forming agent, is replaced by trimethylsiloxysilicic acid, an oil-based cosmetic excellent in the effective washing out with warm water and water resistance was obtained.

Accordingly, in the oil-based cosmetic of the present invention, it is necessary that (b) siliconized pullulan and/or trimethylsiloxysilicic acid is blended.

Furthermore, when used as an oil-based eyelash cosmetic, it is preferable to blend a siliconized pullulan with consideration of the curling effect.

In here, formulation examples of the oil-based cosmetic of the present invention will be illustrated. It is to be understood that the present invention is not limited by these formulation examples.

Formulation Example 1: Oil-Based Mascara

| Formulation Example 1: Oil-based mascara | |
|---|---|
| POE(35)POP(40) dimethylether | 10% by mass |
| Tri(trimethylsiloxy)silylpropylcarbamic acid-pullulan | 3 |
| Isododecane | 7 |
| Hydrophobized iron oxide (black) | 10 |
| Polyacrylate ester emulsion | 18 |
| Solid paraffin | 8 |
| Light isoparaffin | 30 |
| Sorbitan sesquiisostearate | 4 |
| Purified water | 10 |
| Preservative agent | proper quantity |
| Perfume | proper quantity |

Formulation Example 2: Oil-based mascara

| | |
|---|---|
| POE(50)POP(40) dimethylether | 20% by mass |
| Trimethylsiloxysilicic acid | 2 |
| Isododecane | 2 |
| Hydrophobized iron oxide (black) | 10 |
| Polyacrylate ester emulsion | 16 |
| Polyethyleneglycol 1500 | 8 |
| Solid paraffin | 8 |
| Light isoparaffin | 20 |
| Sorbitan sesquioleate | 4 |
| Purified water | 10 |
| Preservative agent | proper quantity |
| Perfume | proper quantity |

Formulation Example 3: Blusher

| | |
|---|---|
| POE(35)POP(40) dimethylether | 1.5% by mass |
| POE(14)POP(7) dimethylether | 1.5 |
| Tri(trimethylsiloxy)silylpropylcarbamic acid-pullulan | 10 |
| Trimethylsiloxysilicic acid | 3 |
| Isododecane | 5 |
| Decamethylcyclopentasiloxane | 10 |
| Methyltrimethicone | 15 |
| Polyethyleneglycol 400 | 3 |
| PEG-10 dimethicone | 3 |
| PEG-20 hydrogenated castor oil triisostearate | 2 |
| Dextrin palmitate | 8 |
| Dextrin (palmitate/octanoate) | 1 |
| Octylsilane-treated triiron dioxide | 2 |
| Octylsilane-treated iron oxide | 1 |
| Octylsilane-treated iron oxide | 0.2 |
| Red 226 | 0.5 |
| Distearyldimonium hectorite | 5 |
| 1,3-butylene glycol | 2 |
| Purified water | 2 |
| L-arginine | 0.1 |
| Sodium hyaluronate | 0.01 |
| Rutile type titanium oxide-covered silica | 5 |
| Iron oxide-covered silica | 2 |
| Octylsilane-treated black iron oxide-covered mica | 1 |
| Light isoparaffin | balance |

Formulation Example 4: Eye shadow

| | |
|---|---|
| POE(35)POP(40) dimethylether | 2% by mass |
| POE(14)POP(7) dimethylether | 2 |
| Tri(trimethylsiloxy)silylpropylcarbamic acid-pullulan | 8 |
| Trimethylsiloxysilicic acid | 1 |
| Methyltrimethicone | 15 |
| Polyethyleneglycol 400 | 1 |
| PEG-10 dimethicone | 4 |
| PEG-20 hydrogenated castor oil triisostearate | 1 |
| Dextrin palmitate | 5 |
| Dextrin (palmitate/octanoate) | 3 |
| Octylsilane-treated triiron dioxide | 3 |
| Octylsilane-treated iron oxide | 5 |
| Red 226 | 0.5 |
| Distearyldimonium hectorite | 3 |
| 1,3-butylene glycol | 1 |
| Purified water | 1 |
| Phellodendoron Amurense extract | 0.5 |
| Rutile type titanium oxide-covered silica | 3 |
| Iron oxide-covered silica | 2 |
| Octylsilane-treated black iron oxide-covered mica | 2 |
| Titanium mica | 10 |
| Colcothar-covered mica | 15 |
| Light isoparaffin | balance |

Formulation Example 5: Nail enamel

| | |
|---|---|
| POE(35)POP(40) dimethylether | 5% by mass |
| POE(14)POP(7) dimethylether | 1 |
| Tri(trimethylsiloxy)silylpropylcarbamic acid-pullulan | 15 |

| | |
|---|---|
| Trimethylsiloxysilicic acid | 3 |
| Isododecane | 3 |
| Methyltrimethicone | 30 |
| Polyethyleneglycol 400 | 1 |
| PEG-10 dimethicone | 2 |
| PEG-20 hydrogenated castor oil triisostearate | 1 |
| Dextrin palmitate | 3 |
| Dextrin (palmitate/octanoate) | 1 |
| Distearyldimonium hectorite | 5 |
| 1,3-butylene glycol | 2 |
| Purified water | 2 |
| L-arginine | 0.1 |
| Sodium hyaluronate | 0.01 |
| Rutile type titanium oxide-covered silica | 1 |
| Iron oxide-covered silica | 1 |
| Octylsilane-treated black iron oxide-covered mica | 1 |
| Polyethylene terephthalate/aluminum/epoxy laminated powder | 10 |
| Light isoparaffin | balance |

Formulation Example 6: Lip gross

| | |
|---|---|
| POE(35)POP(40) dimethylether | 3% by mass |
| POE(14)POP(7) dimethylether | 1.5 |
| Tri(trimethylsiloxy)silylpropylcarbamic acid-pullulan | 8 |
| Trimethylsiloxysilicic acid | 2 |
| Isododecane | 10 |
| Candelilla wax | 2 |
| Diisostearyl malate | 10 |
| Liquid paraffin | 10 |
| Heavy liquid isoparaffin | 10 |
| Squalane | 2 |
| δ-tocopherol | 0.05 |
| Polyethyleneglycol 400 | 1.5 |
| PEG-10 dimethicone | 1 |
| PEG-20 hydrogenated castor oil triisostearate | 2 |
| Dextrin palmitate | 3 |
| Dextrin (palmitate/octanoate) | 7 |
| Distearyldimonium hectorite | 3 |
| 1,3-butylene glycol | 1.5 |
| Purified water | 0.5 |
| Sodium hyaluronate | 0.01 |
| Rutile type titanium oxide-covered silica | 1 |
| Iron oxide-covered silica | 1 |
| Octylsilane-treated black iron oxide-covered mica | 1 |
| Carmine-covered titanium mica | 0.5 |
| Dye | proper quantity |
| Perfume | proper quantity |
| Methyl trimethicone | balance |

What is claimed is:

1. An oil-based cosmetic, comprising:
(a) 1 to 25 mass % of a block-type alkylene oxide derivative having a chemical formula (I)

$$R^1O\text{---}[(EO)_p(PO)_q(EO)_r]\text{---}R^2 \qquad (I)$$

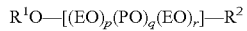

wherein EO is an oxyethylene group and PO is an oxypropylene group; p, q, and r are average addition mole numbers; wherein $p \geq 1$, $r \geq 1$, $10 \leq p+r \leq 70$, and $14 \leq q \leq 60$ ; $R^1$ and $R^2$ are methyl;
(b) 1 to 15 mass % of tri(trimethylsiloxy)silylpropylcarbamyl pullulan and trimethylsiloxysilicic acid;
(c) at most 10% by mass of water;
(d) 10 to 80% by mass of at least one volatile oil;
(e) 1 to 20% by mass of at least one wax;
(f) 1 to 15% by mass of at least one dextrin fatty acid ester; and
(g) 1 to 10% by mass of at least one organic-modified clay mineral;
wherein the cosmetic is removable from skin by washing out with water having a temperature in the range of 35° C. to 45° C.

2. The oil-based cosmetic according to claim 1, further comprising trimethylsiloxysilicic acid.

3. An oil-based eyelash cosmetic comprising: a cosmetic according to claim 1.

4. An oil-based eyelash cosmetic comprising: a cosmetic according to claim 2.

5. A makeup method comprising:
a step of applying a cosmetic according to claim 1 on a skin, and
a step of removing said cosmetic by washing out with water; wherein the temperature of said water is in a range of 35° C. to 45° C.

6. A makeup method comprising:
a step of applying a cosmetic according to claim 2 on a skin, and
a step of removing said cosmetic by washing out with water; wherein the temperature of said water is in a range of 35° C. to 45° C.

7. A makeup method comprising:
a step of applying an oil-based eyelash cosmetic according to claim 3 on an eyelash, and
a step of removing said cosmetic by washing out with water; wherein the temperature of said water is in a range of 35° C. to 45° C.

8. A makeup method comprising:
a step of applying an oil-based eyelash cosmetic according to claim 4 on an eyelash, and
a step of removing said cosmetic by washing out with water; wherein the temperature of said water is in a range of 35° C. to 45° C.

* * * * *

UNITED STATES PATENT AND TRADEMARK OFFICE
CERTIFICATE OF CORRECTION

PATENT NO. : 10,639,268 B2  
APPLICATION NO. : 15/329081  
DATED : May 5, 2020  
INVENTOR(S) : Nozomi Fujiyama et al.

Page 1 of 1

It is certified that error appears in the above-identified patent and that said Letters Patent is hereby corrected as shown below:

In the Claims

Column 16, Line 6, in Claim 1, cancel the text beginning with "and trimethylsiloxysilicic acid"

Signed and Sealed this
Twenty-first Day of July, 2020

Andrei Iancu
*Director of the United States Patent and Trademark Office*